United States Patent
Park et al.

(10) Patent No.: US 10,682,122 B2
(45) Date of Patent: Jun. 16, 2020

(54) IMAGE-BASED USER INTERFACE FOR CONTROLLING MEDICAL IMAGING

(71) Applicant: Siemens Medical Solutions USA, Inc., Malvern, PA (US)

(72) Inventors: Mikyoung Park, Issaquah, WA (US); Rushabh Modi, Sammamish, WA (US); Kutay F. Ustuner, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 934 days.

(21) Appl. No.: 14/958,016

(22) Filed: Dec. 3, 2015

(65) Prior Publication Data
US 2017/0156698 A1 Jun. 8, 2017

(51) Int. Cl.
| | |
|---|---|
| *A61B 8/00* | (2006.01) |
| *G06F 3/0484* | (2013.01) |
| *G06F 3/0482* | (2013.01) |
| *G06F 3/0488* | (2013.01) |
| *A61B 8/08* | (2006.01) |

(52) U.S. Cl.
CPC ............ *A61B 8/467* (2013.01); *A61B 8/463* (2013.01); *A61B 8/5269* (2013.01); *A61B 8/54* (2013.01); *G06F 3/0482* (2013.01); *G06F 3/0488* (2013.01); *G06F 3/04845* (2013.01); *G06F 3/04847* (2013.01); *A61B 8/481* (2013.01); *A61B 8/485* (2013.01); *A61B 8/486* (2013.01); *A61B 8/488* (2013.01); *A61B 8/5261* (2013.01)

(58) Field of Classification Search
CPC ......... A61B 8/463; A61B 8/467; A61B 8/481; A61B 8/485; A61B 8/486; A61B 8/488; A61B 8/5261; A61B 8/5269; A61B 8/54; G06F 3/0482; G06F 3/04845; G06F 3/04847; G06F 3/0488
See application file for complete search history.

(56) References Cited

U.S. PATENT DOCUMENTS

| | | | |
|---|---|---|---|
| 5,919,138 A | 7/1999 | Ustuner | |
| 8,526,669 B2 | 9/2013 | Lavin et al. | |
| 2004/0267124 A1* | 12/2004 | Roundhill | A61B 8/465 600/443 |
| 2007/0130515 A1* | 6/2007 | Maas | G06T 19/00 715/201 |
| 2009/0252429 A1 | 10/2009 | Prochazka et al. | |
| 2010/0095340 A1 | 4/2010 | Ei et al. | |
| 2012/0157843 A1* | 6/2012 | Lavin | A61B 8/465 600/443 |

(Continued)

FOREIGN PATENT DOCUMENTS

| | | |
|---|---|---|
| CN | 1846250 A | 10/2006 |
| CN | 103608842 A | 2/2014 |

(Continued)

OTHER PUBLICATIONS

Office Action for Corresponding Korean Application No. 10-2016-0162928 dated Jul. 20, 2018, with English translation.

*Primary Examiner* — Amelie R Davis (57) ABSTRACT

An image-based user interface is used for controlling medical imaging. A variety of images of a same region but associated with different settings are displayed to the user. The user selects the desired image. The medical imager is then configured with the settings from the selected image for imaging a patient.

10 Claims, 2 Drawing Sheets

(56) References Cited

U.S. PATENT DOCUMENTS

2013/0253317 A1* 9/2013 Gauthier ................ A61B 8/468
600/437

FOREIGN PATENT DOCUMENTS

| JP | 2014523772 | 9/2014 |
| KR | 101250490 | 4/2013 |
| WO | 2012176100 | 12/2012 |

* cited by examiner

IMAGE-BASED USER INTERFACE FOR CONTROLLING MEDICAL IMAGING

BACKGROUND

The present embodiments relate to control in medical imaging. In particular, a user interface is provided for control of medical imaging.

Medical imagers include a large number of controls. In ultrasound, gain, frequency, line density, persistence, smoothing, power, gray levels, speckle reduction, edge enhancement, and dynamic range are a few examples of the many parameters that may be controlled. The large number of controls available to the user may slow exam times and introduce complication. Changing a value for one control may result in a need to change the value for a different control. Given the large number of controls, some of which are dependent on each other and some of which are not, configuring the imager may result in frustration. The iterative adjustment of different controls may lead to an undesired image where determining which controls to adjust for a more desired image is not intuitive.

User controls in an ultrasound system give users the flexibility to change the detail resolution, contrast resolution, temporal resolution, penetration, or aesthetics of the image. Unfortunately, current user interfaces are not simple and intuitive for users to choose proper combination of system settings, resulting in poor image quality. Previous attempts to solve this problem have typically involved user control placement with selection ranges in numbers on a control panel and/or touch panel. Automation may control some parameters, but may not provide comprehensive settings and may not provide settings desired by a given user.

BRIEF SUMMARY

By way of introduction, the preferred embodiments described below include systems, methods, computer-readable media, and user interfaces for controlling medical imaging. A variety of images of a same region but associated with different settings are displayed to the user. The user selects the desired image. The medical imager is then configured with the settings from the selected image for imaging a patient.

In a first aspect, a method is provided for controlling medical imaging. Multiple ultrasound images of an internal region are displayed on a display simultaneously. Each of the multiple ultrasound images has a different set of generation parameters such that each of the multiple ultrasound images has a different appearance. User selection of a first of the multiple ultrasound images is received with a user input device. An ultrasound scanner is configured as a function of the generation parameters of the first of the multiple ultrasound images in response to the receiving of the user selection. An ultrasound image of a patient is generated with the ultrasound scanner as configured as the function of the generation parameters.

In a second aspect, a system is provided for controlling a medical scanner. An ultrasound imager includes a display with a plurality of images. The images of the plurality are generated with different values of a first variable. A user input is configured to receive an input of a selection of one of the images of the plurality. A processor is configured to set the value of the first variable as the value from the selected one of the images. The ultrasound imager is configured to generate a representation of a patient with the value of the first variable set as the value from the selected one of the images.

In a third aspect, a non-transitory computer readable storage medium has stored therein data representing instructions executable by a programmed processor for controlling medical imaging. The storage medium includes instructions for: presenting a set of images displayed simultaneously on a monitor where the images are differently processed versions of common input data; receiving a user input of a choice of processing based on selection of one of the images of the set; and setting one or more parameters of an image processor as a function of the choice, the one or more parameters varying the contrast, contrast resolution, detail resolution, penetration, or combinations thereof.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An intuitive image-based user interface controls medical imaging. Instead of relying just on control knobs, buttons or menus with alphanumeric characters or pictograms, a set of images each corresponding to a different set of image processing parameters applied on a common input data are displayed. Candidate images may be displayed in an image matrix with various shapes (e.g., rectangle, triangle, etc.) and size (e.g., 3×3, 4×4, etc.). Each axis of the image matrix may correspond to various imaging quality aspects, such as detail resolution, contrast resolution, temporal resolution, penetration, or aesthetics. The user picks one of the images from the set based on the desired outcome (i.e., appearance). The selection determines the image processor parameters for the examination until a different selection is made. Image parameters associated with the selected image are applied.

In one embodiment, a user interface is provided for medical ultrasound imaging. A set of images are displayed simultaneously on a monitor where all images are differently processed versions of common input data. The common input data is a CINE captured clip or image, or a clip or image selected from a review database. The set of images are organized in a 1XL vector or M×N matrix, where L, M, and N are 2 or higher. The images are B-Mode, Color Doppler, Spectral Doppler, M-Mode, acoustic radiation force impulse, shear wave velocity imaging, contrast enhanced ultrasound, or other ultrasound images. The set of images may be exemplary images representing varying degrees of detail resolution, contrast resolution, temporal resolution, penetration, and/or image aesthetics. Users communicate a choice of processing by picking, such as on a touch monitor, one of the displayed set of images. A system varies one or more parameters of its image processor as a function of the image selected by the user. The parameters vary detail resolution, contrast resolution, temporal resolution, penetration, or image aesthetics for subsequently generated images.

Figure 1:
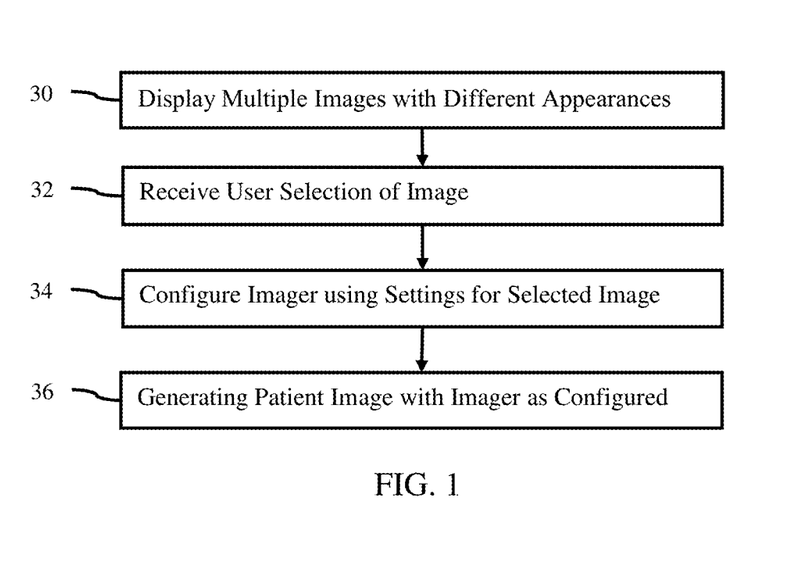
FIG. 1 is a flow chart diagram of one embodiment of a method for controlling medical imaging.

FIG. 1 shows one embodiment of a method for controlling medical imaging. In general, different images created with different values of one or more parameters are simultaneously displayed. Due to the different values, the appearance of the different images varies. By selecting the image with a desired appearance, the user indicates the desired configuration of the imaging system. The imaging system then generates one or more images of a patient using the values or set of settings from the selected image.

Figure 3:
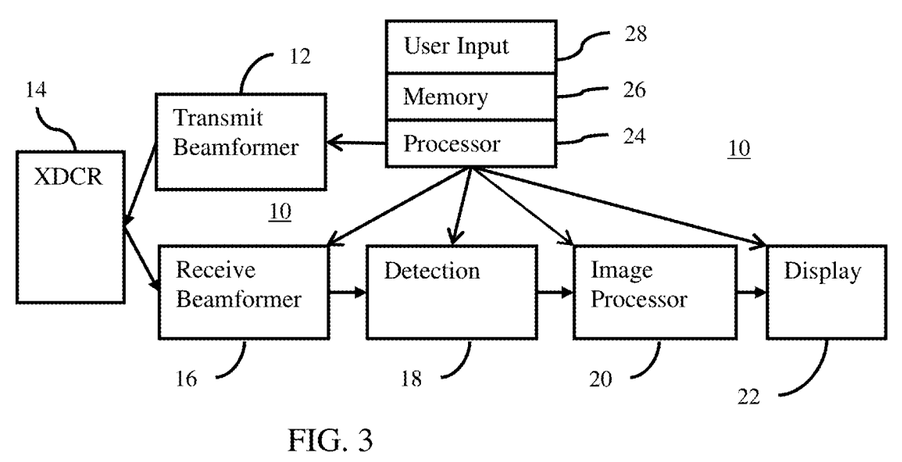
FIG. 3 is a block diagram of one embodiment of a system for control in medical imaging.

The method is performed by the ultrasound system 10 shown in FIG. 3 or a different system. For example, a medical diagnostic ultrasound imaging system generates the multiple-image user interface and generates the image of the patient using the settings from the selected image. The user input receives the user selection of the image displayed on the display. A processor configures any or all of the components of the ultrasound system to generate an image. In alternative embodiments, the imager or medical system is a magnetic resonance, computed tomography, x-ray, fluoroscopy, angiography, positron emission tomography, single photon emission computed tomography, or other now known or later developed medical scanner. The settings are ones appropriate for the type of medical imager.

The acts are performed in the order shown or another order. Additional, different or fewer acts may be used. For example, acts 34 and 36 are combined to be one act. As another example, an act for selecting an imaging application (e.g., cardiac or fetal imaging), selecting a mode of imaging, and/or for initially navigating the imaging to the desired region of the patient are provided in order to determine which set of images to display in act 30. In another example, an act for triggering or activating the user interface when desired is provided. Other acts for configuring the range, variance of interest, number of images, or other aspects of the multiple-image display may be provided.

In act 30, the medical imaging system displays multiple images on a display. For an ultrasound imaging system or scanner, multiple ultrasound images are displayed. A set of images are presented to the user at a same time. Each of the images represents a same internal region. For example, the images are of the same field of view within a current or past patient.

This simultaneous display provides two or more images on a monitor. Any number of images may be displayed, such as two, three, four, six, nine, or other number. The images are adjacent each other without overlap, but may overlap. The images are displayed in a grid pattern, such as a 1×N or N×M arrangement where N and M are integers greater than 1. A rectangular or square grid is used, but triangular, hex, or other grid formats may be used. The images are rectangular, but triangular, hex, or other outlines or borders for the images may be used.

Figure 2:
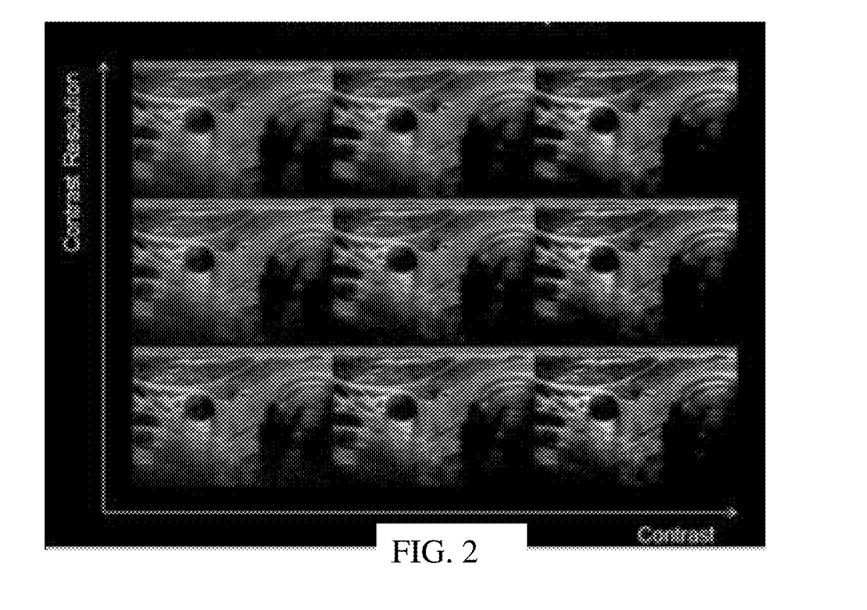
FIG. 2 illustrates an example display of different images generated with different values of control variables.

FIG. 2 shows an example rectangular grid with nine images simultaneously displayed. The images touch each other, but a gap, border or separation may be provided.

The images represent the same internal region. The internal region is of a current patient. For example, the patient is scanned once and the resulting data is processed differently to generate the images. As another example, the patient is scanned differently to generate the different images of the same internal region. Alternatively, the internal region is of a past patient, phantom, or other object. The images are loaded from a database providing representative images for different settings. Different sets of images may be used for different applications, such as different sets for different imaging applications and/or modes (e.g., cardiac, harmonic, contrast, or by imaging mode). User input of a given imaging application or processor detection of the object currently being scanned is used to select the set of images for loading from memory. The set of images most similar to a scan to be performed or currently being performed for a given patient are loaded from the database.

In one embodiment, the images are differently processed versions of common input data. Scan data is acquired. The scan data is processed differently to generate the different images. In other embodiments, the internal region is common, but the data used for the different images is different. For example, scanning is repeated with different beamformer settings to acquire different sets of data for generating at least some of the different images.

The different images have different combinations or sets of generation parameters. By varying the settings, the multiple images have different appearances. One or more settings are the same, such as the type or mode of imaging. For example, all of the images are B-mode, color Doppler, spectral Doppler, M-mode, acoustic radiation forced imaging, shear wave imaging, or contrast agent imaging. The images may all be a same combination of more than one mode, such as color or flow image overlaid on a B-mode image. In alternative embodiments, the type of mode varies between at least some of the images.

One or more settings are different. Any combination of differences may be used. For example, each of the images is different in only one setting. A value for a variable is different for each of the images (e.g., infinite impulse response temporal filtering weight of 0.3-0.9 in 0.1 steps). In other examples, combinations of settings vary. The values for two or more variables are altered between the images (e.g., filter cut off frequency of 2 kHz to 10 kHz and various of 3 different gray scale maps). Some images may be associated with only varying one variable while others are associated with varying more variables. Any combination of variance and/or range of variance may be used for the simultaneously displayed images.

Any image generation parameters may be varied. An image generation parameter is a setting of the imaging system used to generate an image. In ultrasound, the generation parameter may be a scan parameter, such as frequency, line density, scan format, acoustic intensity, steering angle, depth, or other beamformer parameter. The generation parameter may be a post-processing or image processing parameter, such as a variable changed after beamformation and/or detection. Some example post-processing generation parameters include dynamic range, map selection (e.g., which gray or color scale), edge enhancement (e.g., binary or type), temporal filtering, spatial filtering, or combinations thereof. Any variable that may be set in an imaging system may be varied. Any combination of variables may be varied while none, one, or more variables are not varied between any given pair of images and/or through all of the simultaneously displayed images.

In a B-mode imaging example, any of various variables may be set differently to generate the different images being displayed. To scan a field of view with ultrasound, transmit and receive beams are formed by an ultrasound system. The responsive data represents samples in the field of view. The scanning is in any format, such as sector, linear, or vector.

The transmit and/or receive beam characteristics may be set or responsive to parameters. The depth and/or lateral extent of the field of view for the B-mode imaging is set. Similarly, the transmit beam focal depth, transmit frequency, receive frequency, line density, transmit waveform (e.g., number of cycles and/or envelope shape), frame rate, and/or other scanning characteristics are set. The number of transmit focal positions per scan line (e.g., one or two) may be set. Different, additional, or fewer scan (e.g., transmit and receive) parameters may be used.

Data received from the scanning is detected. A B-mode detector determines the intensity of acoustic echoes represented by the received data. For example, the receive data is formatted as in-phase and quadrature data. A square root of a sum of the squares of the in-phase and quadrature terms is calculated as the intensity. Other measures of the magnitude of the acoustic echo may be used for B-mode detection.

Other B-mode processing may be performed based on values for parameters. For example, the detected B-mode data is spatially filtered. One or more parameters may establish the amount, type, or other filtering characteristic. As another example, a sequence of frames from a corresponding sequence of scans of the entire field of view is acquired. Different pairs or other sized groupings of the resulting B-mode frames of data are temporally filtered. Infinite impulse or finite impulse response filtering may be used. One or more parameters may establish the amount, type, or other filtering characteristic. In another example, a general or overall gain is applied. One or more parameters may establish the overall gain. Additionally or alternatively, depth dependent gains may be applied. Different, additional, or fewer B-mode processing parameters may be used, such as setting the dynamic range, edge enhancement, or speckle reduction.

After processing, the detected B-mode data is scan converted, if needed, and mapped using one of various available gray scale maps. A B-mode image is generated. The B-mode image represents the intensity or strength of return of acoustic echoes in the B-mode field of view. The intensities or B-mode data are mapped to gray scale within the dynamic range of the display. The gray scale may be equal or similar red, green, blue (RGB) values used by the display to control pixels. Any color or gray scale mapping may be used. One or more parameters may control the mapping.

Other settings may be available for B-mode or other modes of ultrasound imaging. The values of any of the variables may be different for the different images. For example, the edge enhancement filtering applied is different in each of the different images, but values of other variables are constant.

The variance results in images with different appearances. The value or combination of values may be systematically varied over a range, such as using a common step size dividing a range or combination of ranges by the number of simultaneously displayed images. In other embodiments, the variance provides similar transitions in appearance where a given transition between two images may have a different step size of a variable than for a transition between two other images.

FIG. 2 shows the images having transitions in appearance. The transition may be across all of the images (i.e., each image is altered with respect to one characteristic). In the example of FIG. 2, two characteristics are varied (e.g., contrast and contrast resolution). Three or more characteristics may be varied. The degree of contrast, contrast resolution, detail resolution, penetration, or combinations thereof are varied. In FIG. 2, two characteristics are varied along the two axes. The variance may not be mapped to the image grid in other embodiments. Any number of variables may be varied to provide the transition in the desired characteristic. The characteristic may not be labeled on the display.

In one embodiment, the settings used by different experts are captured. Rather than mapping step size in characteristic and/or step size in values, different combinations of settings based on study or experimentation are used. Other experience-based or default variance of values of variables may be used.

The images are static. Alternatively, the images represent on-going or previously acquired clip or sequence. By each image being at a same point in the sequence but showing the sequence, the image with the desired appearance at a given point in a sequence (e.g., heart cycle) or throughout the sequence may be identified by the user.

The user may manually alter one or more values. As a result, the images are all re-processed to be generated with the altered value. One or more images may be the same if the manually altered value is the only value varying between two images. In other embodiments, any manual alteration occurs after user selection of a given image. In yet another alternative, control that is more refined is provided. A first set of images is output. After selection of one image, another set of images with more refined (e.g., smaller step sizes) around the selected values are generated for user selection.

In act 32, a user input receives user selection of one of the multiple images. For example, a touch screen receives user selection of an image. A mouse, track ball, and/or touch pad with user selection once a cursor is positioned over an image may instead be used. Other user inputs may be used.

The user selects one of the images. For example, the user selects the center image in the left row in the example of FIG. 2. By touching or selecting anywhere within an image, the user selects that particular image. In alternative embodiments, the user selects more than one image. The images are selected in sequence, and the values for the selected images are averaged. Alternatively, a relative distance between boarders or centers of two or more images is used to indicate a relative weighting in interpolation to derive values for the variables between the two or more images.

The user selects the image with a desired appearance. The different images have different appearance due to the variation in the values or characteristic. By viewing the set of images, the user may quickly and easily decide upon a combination of values of image generation parameters that results in a desired appearance or has a desired degree of a given characteristic. The selection indicates the desired configuration for imaging a patient. As compared to individually adjusting the many controls into various possible combinations, image selection may reduce the user inputs or option selections by a factor of 10, 100, or 1000. Some user setting of individual controls may be provided, such as setting acquisition parameters based on an application or manual control where the image-based user interface is used to set image processing parameters.

In act 34, the ultrasound scanner or imager is configured based on the selection. A processor controls the ultrasound scanner. The image generation parameters are set for operation of the scanner to image a patient. The values of the image generation parameters are set as a function of the values of the image generation parameters used for the selected image. The same values are used. Alternatively, the values are used with other values to configure the scanner.

For example, the values are interpolated with values of another selected image to derive the settings of the generation parameters. As another example, only a sub-set of the values from the selected image is used and default or user set values are used for other parameters.

The configuration occurs in response to the user selection of the image. Selection of the image triggers configuration of the scanner or imager. Other triggers may be used, such as configuring after user confirmation of the selection.

The setting of the parameters of the image processor, imager, or scanner as a function of the choice of images more likely provides for images with a desired contrast, contrast resolution, detail resolution, penetration, appearance, or combinations thereof. The setting of the parameters to the values of the selected image provides for a similar appearance in the generated images. Where the multiple images for selection are of the patient, the configured imager more likely generates images with a same appearance. Where the multiple images for selection are loaded from a database based on the application or internal region to be scanned, the configuration causes the imager to generate images with similar appearance, but some patient-specific differences may lead to a difference in appearance. The user may manually adjust one or more parameters or may select a different image. By configuring, one or more image generation parameters used for subsequent or continuing imaging are set and/or changed.

In act 36, the imager generates an image of the patient. In ultrasound, the ultrasound scanner generates an ultrasound image of the patient. The imager is configured using the values of the parameters from the selected image. The multiple images act as a user interface for configuring the imager. The imager then operates to generate one or more images of a patient as configured. For example, the imager is configured in a same way (i.e., same values of parameters) as the selected image. The image or sequence of images is generated with the imager as configured. Rather than displaying a grid or matrix of images simultaneously, the image or images appropriate for the selected imaging mode are displayed full size as part of diagnostic imaging of the patient.

The appearance and/or characteristics of the generated images are the same or similar to the selected image and may be more different than unselected ones of the images. In the B-mode example, a B-mode image is generated. The B-mode image is generated after the setting of the one or more B-mode parameters. All, some, or none of the previously used settings are used for the subsequent imaging. For example, one, two, or three B-mode parameters are changed to match the values for the selected image, and other B-mode parameters are maintained the same to match the selected image. B-mode imaging with the new combination of values for the B-mode parameters is performed. The ultrasound imaging system scans, processes, and generates an image for B-mode imaging based on the B-mode parameters. A sequence of images using the same settings may be generated.

FIG. 3 shows one embodiment of a system 10 for controlling a medical scanner. The system 10 generates sample images with different settings. By selecting one or more of the images, the user indicates the desired appearance. The settings to provide that desired appearance are mapped from the settings of the selected image. The system 10 is configured based on the user-selected image or images for subsequent imaging.

The system 10 is an ultrasound imager. In one embodiment, the ultrasound imager is a medical diagnostic ultrasound imaging system. In alternative embodiments, the ultrasound imager is a personal computer, workstation, PACS station, or other arrangement at a same location or distributed over a network for real-time or post acquisition imaging. In yet other embodiments, the system 10 is a magnetic resonance, computed tomography, x-ray, fluoroscopy, angiography, positron emission tomography, single photon emission computed tomography, or other medical imaging system.

The system 10 implements the method of FIG. 1 or other methods. For example, the system 10 generates the images with different values for one or more variables on the display 22. The user input 28 receives user selection of one of the images. The processor 24 configures the system 10 to image using the values of the variables for the selected image.

The system 10 includes a transmit beamformer 12, a transducer 14, a receive beamformer 16, a detector 18, an image processor 20, a display 22, a processor 24, a memory 26, and a user input 28. Additional, different or fewer components may be provided. For example, the receive beamformer 16 through the display 22 represents an ultrasound processing path of an ultrasound imager. Other components may be provided in the path, such as a spatial filter, a scan converter, a mapping processor for setting dynamic range, or an amplifier for application of gain. While the processor 24 is shown for controlling the transmit beamformer 12, the receive beamformer 16, the detector 18, the image processor 20, and the display 22, fewer, different, or additional components may be controlled. Other control devices or structures may be used.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing to focus a resulting beam at one or more depths. The waveforms are generated and applied to a transducer array with any timing or pulse repetition frequency. For example, the transmit beamformer 12 generates a sequence of pulses for different lateral and/or range regions. The pulses have a center frequency.

The transmit beamformer 12 connects with the transducer 14, such as through a transmit/receive switch. Upon transmission of acoustic waves from the transducer 14 in response to the generated waves, one or more beams are formed during a given transmit event. The beams are for imaging. Sector, Vector®, linear, or other scan formats may be used. The same region is scanned multiple times for generating a sequence of images.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms, and connects with the receive beamformer 16 for converting acoustic echoes into electrical signals. The transducer 14 transmits the transmit beams where the waveforms have a frequency and are focused at a tissue region or location of interest in the patient. The acoustic waveforms are generated in response to applying the electrical waveforms to the transducer elements. The transducer 14 transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms. The sampling by the receive beamformer 16 is for a range of depths. Timing is used to select the range of depths over which the sampling occurs.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band.

The receive beamformer 16 outputs beam summed data representing spatial locations. Data for a single location, locations along a line, locations for an area, or locations for a volume are output. The data is for B-detection.

The processor 24 and/or a separate beamformer controller configure the beamformers 12, 16. By loading values into registers or a table used for operation, the values of acquisition parameters used by the beamformers 12, 16 for imaging are set. Any control structure or format may be used to establish the imaging sequence. The beamformers 12, 16 are caused to acquire data for imaging at a frame rate, with a transmit focus, at an imaging frequency band, over a depth, and/or with a resolution. Different values of one or more acquisition or scanning parameters may result in a different frame rate, signal-to-noise ratio, penetration, and/or resolution.

The detector 18 is a B-mode, Doppler, flow mode, spectral Doppler, or other detector. As a B-mode detector, the detector 18 detects intensity from the beamformed samples. Any B-mode detection may be used. In one embodiment, the B-mode detector is a general processor, application specific integrated circuit, or field programmable gate array. Log compression may be provided by the B-mode detector so that the dynamic range of the B-mode data corresponds to the dynamic range of the display.

The image processor 20 is a processor, analog circuit, digital circuit, application specific integrated circuit, field programmable gate array, or other filter for temporal filtering. For example, the image processor 20 provides buffers or memories for storing frames of data and weights, multipliers for weighting the frames, and a summer for summing the weighted frames. The image processor 20 provides temporal filtering, spatial filtering, edge enhancement filtering (e.g., directional filters), dynamic range mapping, amplitude adjustment, equalizing, gray scale or color mapping, or other image processing. Any post-acquisition or post-scan processing and corresponding parameters may be implemented by the image processor 20.

The display 20 is a CRT, LCD, monitor, plasma, projector, printer, or other device for displaying an image or sequence of images. Any now known or later developed display 20 may be used. The display 20 displays two-dimensional images or three-dimensional representations. The display 20 displays one or more images representing the scan region.

The spatial resolution, contrast, contrast resolution, temporal resolution, penetration, appearance, and/or image quality is based, in part, on the acquisition or processing parameters. The ultrasound imager using different values for the acquisition and/or processing parameters may result in different spatial resolution, contrast, contrast resolution, temporal resolution, penetration, appearance and/or image quality for the displayed image. Different transmit frequencies tradeoff between penetration depth, signal-to-noise ratio, and resolution. Different persistence trades off between signal-to-noise ratio and temporal resolution. A difference in values of parameters may result in images having different spatial resolution, contrast, contrast resolution, temporal resolution, penetration, and/or image quality (e.g., signal-to-noise ratio).

The system 10 presents a plurality of images associated with different values of one or more parameters. One variable is set differently in each or in some of the images of the plurality. Other variables are set differently or the same in the same or others of the images. Any combination of values is used for a given image. Each image has at least one value for at least one variable that is different from all or some others of the images. Each image has a combination of values unique to that image. Two or more images may be identical, such as copying or using the same values, but at least two images use different combinations of values for the same variables.

The images of the plurality are generated using common data in one embodiment. The patient is scanned to provide the common data as beamformed or detected data. The values of the post-processing or image processing variables are varied to provide the different images. In other embodiments, the patient is scanned separately for the different images, such as where values of one or more acquisition parameters are changed.

In other embodiments, the images with the different value sets represent scans of another patient or object. The application or other user input may be used to define the set of images to be presented, such as using the internal region to be scanned, the patient weight, and/or age of the patient to select a set of images from a database.

The images of the plurality are simultaneously displayed adjacent each other, such as in a grid. The user may view the differences in appearance by visually comparing the adjacent images. These differences in appearance are mapped to or represent the differences in the sets of values of the parameters used to create the images. The difference in appearance may be due to differences in any characteristic, such as the images having varying contrast, contrast resolution, detail resolution, penetration, or combinations thereof due, at least in part, to the different values for one or more variables.

The ultrasound imager includes, interacts with, or is controlled by the processor 24. The processor 24 is part of a control system of the ultrasound imager or is a separate computer. The memory 26 and user input 28 are shown as associated with the processor 24, but may alternatively or additionally be part of the ultrasound imager.

The user input 28 is a track ball, mouse, joy stick, touch pad, buttons, slider, knobs, position sensor, touch screen, combinations thereof or other now known or later developed input devices. The user input 28 is operable to receive a selected point, image, or other information for controlling imaging by user setting of image generation parameters. For example, the user clicks on one of the images of the plurality. The image with the desired appearance is selected using the user input 28. The combination of values of the parameters for the selected image is used instead of the combination of values for unselected images. In another example, the user rotates a knob or moves a slider to highlight different ones of the images of the plurality for selection.

The user input 28 is part of a user interface with the plurality of images. The hardware and/or software of the user interface configure the user input 28 to receive inputs from the user and relate those inputs to specific images and/or corresponding values of image generation parameters. The user input 28 is configured to receive an input of a selected image. This received information is used to determine a combination of values of parameters.

The processor 24 is a control processor, general processor, digital signal processor, graphics processing unit, application specific integrated circuit, field programmable gate array, network, server, group of processors, data path, combinations thereof, or other now known or later developed device or devices for operating the user interface and configuring the system 10 for imaging. The processor 24 is configured by software and/or hardware to perform the acts.

The processor 24 is configured to configure the system 10. Based on the user selection of an image from the set of images, the values of the parameters of the beamformers 12, 16, detector 18, image processor 20, and/or other components of the ultrasound imager are set by the processor 24. The values of the parameters are calculated by look-up, derived from the values used for the selected image, or are the values used for the selected image. The values of the parameters are loaded into buffers and/or communicated to components for operating the system 10. The processor 24 sets the values of the variables as the values or as a function of the values from the selected image or images. At least one, a sub-set, or all of the variables for acquisition and/or image processing use values derived from the selected image of the multi-image user interface.

The processor 24 causes the ultrasound imager as configured to generate and output one or more images. Once the parameters are set, the system 10 scans the patient and generates one or more images from the scan as part of diagnostic imaging. The set values for the image generation parameters cause the ultrasound system 10 to acquire and/or process ultrasound data representing the patient. The acquired and processed ultrasound data is output as an image or other representation (e.g., graph, quantity, image, or three-dimensional rendering) of the patient on the display 20. The images are generated with the values for the variables set based, at least in part, on the selected image.

The image generation may be on going, such as repeated in real time (e.g., 20 Hz frame rate or greater) or periodically. Alternatively, a single representation is generated. The ultrasound system 10 as configured due to the image selection is used with the configuration until re-configured. The user may manually adjust one or more values. The processor 24 may automatically adjust one or more values. Other values may be maintained as set based on the image selection. The ultrasound system 10, as partially configured due to the image selection, continues to generate images of the patient. At some point, all of the values or all of the values based on the image selection may be replaced. Alternatively, the user navigates the user interface to repeat the image selection in order to reconfigure the ultrasound system 10. Such repetition may or may not alter the values of all of the variables as currently configured.

The memory 26 stores values for variables to configure the ultrasound imager. The values used for the different images displayed as part of the user interface are stored. The images for display or after display may be stored. The values derived for configuring the ultrasound imager may be stored. Tables of values and/or sets of images may be stored. The memory 26 may be a database organized by sets to provide values and/or images for different applications or circumstances.

The processor 24 and/or the ultrasound imager operate pursuant to instructions stored in the memory 26 or another memory. The instructions configure the system for performance of the acts of FIG. 1. The instructions configure the processor 24 and/or the ultrasound imager for operation by being loaded into a controller, by causing loading of a table of values (e.g., values for a selected image), and/or by being executed. The ultrasound imager is configured to generate a plurality of images with different settings for selection by the user. In response to the user selection of one or more images with different settings, the processor is configured to configure the ultrasound imager based on the settings of the selected image. The processor 24 is configured to use a user indication of an image from a plurality of images to set or alter one or more values for one or more variables. The ultrasound imager is then configured to scan a field of view, process responsive data, and generate an image.

The memory 26 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method of controlling medical imaging, the method comprising:

displaying on a display multiple ultrasound images in a N×M arrangement where N and M are integers greater than 1, the ultrasound images being of an internal region and being displayed simultaneously, each of the multiple ultrasound images having a different set of generation parameters such that each of the multiple ultrasound images has a different appearance in first and second characteristics of detail resolution, contrast resolution, temporal resolution, or penetration, the different appearances in the first characteristic being over a range of values in the first characteristic along N and the different appearances of the second characteristic being a range of values in the second characteristic along M;

receiving user selection of a first of the multiple ultrasound images with a user input device;

configuring an ultrasound scanner as a function of the generation parameters of the first of the multiple ultrasound images in response to the receiving of the user selection; and generating a patient ultrasound image of a patient with the ultrasound scanner as configured as the function of the generation parameters.

2. The method of claim 1 wherein displaying comprises displaying the multiple ultrasound images as ultrasound images of a same mode, the same mode comprising B-mode, color Doppler, spectral Doppler, M-mode, acoustic radiation forced imaging, shear wave imaging, or contrast agent imaging.

3. The method of claim 1 wherein displaying comprises displaying the multiple ultrasound images with the different generation parameters being post-processing parameters.

4. The method of claim 1 wherein displaying comprises creating the multiple ultrasound images of the internal region with scan data common to all of the multiple images.

5. The method of claim 1 wherein displaying comprises creating the multiple ultrasound images of the internal region of the patient.

6. The method of claim 1 wherein displaying comprises loading the multiple ultrasound images of the internal region as images of another patient different from the patient for which the patient ultrasound image is generated, the loading being from a database based on a user selected application for the generating.

7. The method of claim 1 wherein displaying comprises displaying the multiple ultrasound images with the generation parameters being frequency, line density, dynamic range, map selection, edge enhancement, temporal filtering, spatial filtering, or combinations thereof.

8. The method of claim 1 wherein receiving the user selection comprises receiving selection of the first image as a touch on the first image on a touch screen.

9. The method of claim 1 wherein configuring comprises using values of the generation parameters of the first image.

10. The method of claim 1 wherein generating the patient ultrasound image comprises generating the patient ultrasound image and other images of a sequence with the ultrasound scanner as configured.

* * * * *